May 15, 1973 R. S. MOORE Plant Pat. 3,331
MINIATURE ROSE PLANT
Filed May 3, 1971
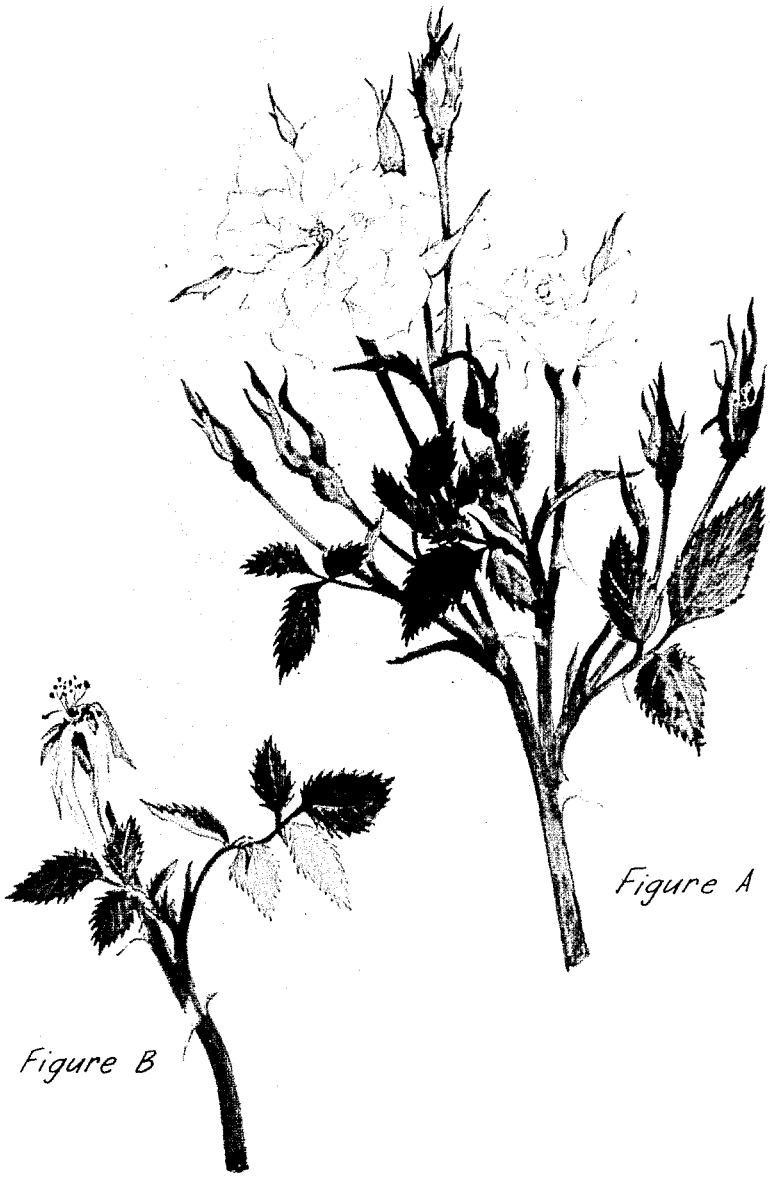
WITNESS
Jeanette Nunn Copley
INVENTOR
Ralph S. Moore

United States Patent Office

Plant Pat. 3,331
Patented May 15, 1973

3,331

MINIATURE ROSE PLANT

Ralph S. Moore, 2519 E. Noble Ave.,
Visalia, Calif. 93277

Filed May 3, 1971, Ser. No. 139,794
Int. Cl. A01h 5/00
U.S. Cl. Plt.—7 1 Claim

The present invention relates to a new and distinct variety of hardy, dwarf, bush type rose plant of the miniature class; the variety being primarily characterized—as to novelty—by buds and flowers of soft to medium yellow color blended or overlaid with shades of orange.

The variety is further characterized by:

An abundance of bloom, with flowers borne singly or several to the stem.

MODERATE FRAGRANCE

A plant which is vigorous, of rounded to spreading habit, and with semi-glossy (or flat) medium small foliage with pointed leaflets; the buds and flowers being similar in size and shape as compared to Yellow Necklace (not patented) miniature rose, with a blending of orange with the yellow color instead of clear yellow. The plant which has a normal height of 10" to 14" at maturity can easily be maintained at 10" or less with occasional trimming.

A plant which grows and blooms satisfactorily both in greenhouse and outdoors; is a good plant for growing in pots; and provides excellent garden decoration as well as cut flowers.

The present variety of miniature rose was originated by me at my nursery located at Visalia, Calif., under conditions of careful control and observation, as a cross between Golden Glow, a climber (U.S. Plant Pat. No. 263, expired) as the seed parent, and Magic Wand, miniature rose (not patented), as the pollen parent.

Subsequent to origination of the variety I successfully asexually reproduced it in my nursery, located as aforesaid, by budding as well as by cuttings; the reproductions having run true in all respects.

The figure of the drawing illustrates a spray, including foliage, buds and flowers.

Referring now specifically to the new and distinct variety of miniature rose plant, the following is a detailed description thereof in outline, all major color plate identifications being by reference to the British Colour Council Horticultural Colour Chart, except where common terms of color definition are employed.

Type: Hardy, dwarf; bush; seedling; greenhouse; outdoors; garden decoration; potted plant.

Class: Miniature.

Flowers: Continuity—continuous; repeat-blooms all season. Fragrance—slight to moderate.

Flowers borne: singly and several together on 3" to 4", sturdy, wire-like stem.

Quantity of bloom: average abundance both outside and in greenhouse.

Bud:

*Peduncle.*—Medium length; erect; light green; with essentially smooth surface.

*Before calyx breaks.*—Size, small.

*Form.*—Long, pointed; with foliaceous appendages and few very short hairs on surface of bud; with foliaceous parts extending beyond the tip of the bud equal to one half or more of its length.

*Color.*—Light to medium green, sometimes lightly tinted reddish or bronze.

*As calyx breaks.*—Color medium yellow (or tinted orange); size—small.

*Form.*—Long pointed, becoming long oval shaped as it opens.

*Opening.*—Usually opens well in all weather.

Bloom: Size when fully open; small, averaging 1½ or under.

*Petalage.*—Double—averaging about 30 petals (often with several additional small petals or petaloids), arranged regularly.

*Form.*—Slightly rounded (high center) at first with petals rolled loosely outward, and later at maturity becoming flat with petals remaining loosely rolled outward and with outer petals rolled more downward.

Petals: Rather thin; moderately stiff; satiny both inside and outside.

*Shape.* — Outside petals — broad lanceolate, with rounded tip; intermediate petals—broad lanceolate, with rounded tip; inside petals—narrow lanceolate, rounded tip.

Color: Newly opened flower from a plant grown indoors in plastic greenhouse (April 1971) Visalia, Calif.

*Outside petal.*—Outside surface—Straw Yellow 604 or 604/1 at base shading lighter, then overlaid or blending into Orange 12/2 on upper ⅓ of petal; inside surface—Straw Yellow 604 at base thence lighter and overlaid or blending into Orange 12/2 on upper ½ of petal;

*Intermediate petal.*—Outside surface—similar to outside petal; inside surface—color similar to outside petal.

*Inside petal.*—Outside surface—similar to intermediate petal; inside surface—similar to intermediate petal. As flowers age petals become lighter in color, the yellow areas becoming Straw Yellow 604/2 (or similar) and the orange becoming Orange 12/3 (or similar). In warmer weather the buds and flowers may be all yellow with little no none of the orange color. High light intensity also tends to make the yellow color predominant. Flower longevity (April 1971)—bush in pot in greenhouse—3–4 days. Cut flowers at living room temperature—2–3 days.

Reproductive organs:

*Stamens.*—Average number; arranged regularly about pistil.

*Filaments.*—Short; of fairly uniform length.

*Pollen.*—Small amount; yellow.

*Pistils.*—Average.

*Styles.*—Pale yellow.

*Ovaries.*—All enclosed in calyx.

*Hips.*—Rare; small; round; orange.

*Sepals.*—Permanent; spear-shaped.

*Seeds.*—Rare; not viable.

Foliage:

*Leaves.*—Compound of five leaflets (occasionally 3 or 7); abundant; medium small; leathery; little or no gloss (flat).

*Leaflets.*—Shape: broad lanceolate; apex acute; base acute to nearly rounded. Margin serrate. Color: light to normal green. Rachis: medium strength; upper side grooved; under side sparsely to moderately thorny. Stipules: medium to long; narrow; short to medium length points, turning out at an angle of about 45 degrees.

Growth:

*Habit.*—Dwarf; bushy; rounded to spreading; much branched.

*Growth.*—Free; vigorous.

*Canes.*—Medium; slender.

*Main stems.*—Color: medium green. Thorns: moderately thorny; medium to long oval base; medium to long; hooked slightly downward; color—brownish.

*Prickles.*—None. Hairs—none.

*Branches.*—Color; medium green. Thorns: moderately thorny; medium to long; hooked slightly downward; medium to long oval base. Prickles—none. Hairs—none.

*New shoots.*—Color: medium green. Thorns: moderately thorny; medium to long; hooked slightly downward; brownish; sharp points; base short to medium, oval.

*Prickles.*—None. Hairs—none.

The miniature rose plant and its flowers as herein described may vary in slight detail due to climatic, soil and cultural conditions under which the variety may be grown; the present description being of the variety as grown at Visalia, Calif.

The following is claimed:

1. A new and distinct variety (cultivar) of a miniature rose plant of hardy, dwarf, rounded, much branched, bush type, as illustrated and described, characterized by bush and flowers resembling the Yellow Necklace miniature rose (not patented) in general size and form, the color generally being deeper yellow with orange shadings, the general color effect of the bud and freshly opened flower being soft orange to gold yellow; and further characterized by a plant which is vigorous and compact in growth, easy to propagate from cuttings, with abundant medium small foliage of a light to medium green color and an abundance of bloom borne almost continuously throughout the growing season with flowers borne singly or several to the stem.

No references cited.

ROBERT E. BAGWILL, Primary Examiner